United States Patent [19]

Nakanishi et al.

[11] Patent Number: 5,008,441

[45] Date of Patent: Apr. 16, 1991

[54] CAFFEIC ACID ESTERS AND METHODS OF PRODUCING AND USING SAME

[75] Inventors: Koji Nakanishi; Eugene M. Oltz, both of New York, N.Y.; Dezider Grunberger, Teaneck, N.J.

[73] Assignee: The Trustees of Columbia University in the City of New York, New York, N.Y.

[21] Appl. No.: 369,060

[22] Filed: Jun. 20, 1989

Related U.S. Application Data

[63] Continuation of Ser. No. 81,649, Aug. 4, 1987, abandoned.

[51] Int. Cl.$^5$ ............................................. C07C 69/76
[52] U.S. Cl. ...................................................... 560/75
[58] Field of Search ........................... 560/75; 514/532

[56] References Cited

PUBLICATIONS

Papay V., et al, Stud. Org. Chem., 1985, pp. 233-240.

*Primary Examiner*—Paul J. Killos
*Attorney, Agent, or Firm*—John P. White

[57] ABSTRACT

The invention relates to a compound having the structure:

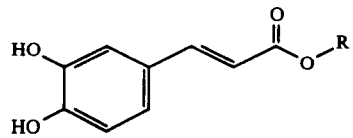

wherein R comprises a phenethyl, butyl, hexyl or ethyl group.

The invention also related to methods of isolating and producing the compound, methods of treating inflammation in a subject and methods of substantially inhibiting the growth of transformed cells in a population of normal and transformed cells.

21 Claims, 6 Drawing Sheets

CAFFEIC ACID ESTERS AND METHODS OF PRODUCING AND USING SAME

The invention described herein was made in the course of work under Grant Nos. CA 2111, CA 31696, and AI 10187 from the National Institute for Health. The U.S. Government has certain rights in this invention.

This application is a continuation of U.S. Ser. No. 081,649 filed Aug. 4, 1987 now abandoned.

BACKGROUND OF THE INVENTION

Throughout this application various publications are referenced and citations are provided in parentheses for them. The disclosures of these publications in their entireties are hereby incorporated by reference into this application in order to more fully describe the state of the art to which this invention pertains.

Propolis, a popular "folk medicine" purported to have therapeutical benefit, is a brownish mass produced by honeybees in their hives. A significant number of so-called "folk medicines" have withstood scientific scrutiny, with many of their purported therapeutic benefits being attributable to distinct chemical entities. Such naturally derived compounds often produce fewer and less serious side effects as compared to analogous man-made pharmaceuticals; unfortunately, most are chemically complex, not lending themselves to economically feasible syntheses. Propolis, is alleged to exhibit a broad spectrum of activities. It is marketed in health stores as a natural antibiotic (F. B. Wells, Am. Bee J. 116, 512 (1976) (a review of the antimicrobial effects of propolis)); aqueous extracts are sold in Europe as a cough syrup and sore throat remedy; compacts prepared from it are used to treat skin inflammations (Apimondia, A Remarkable Hive Product: Propolis, Bucharest, 1978); ingestion of raw propolis is reputed to clear sinuses and treat viral infections (E. L. Chisalberti, Bee World 60, 59 (1979)); and propolis has been used to arrest the growth of tumors. Propolis is a conglomeration of compounds mostly derived from plant sources, and is rich in waxes, resins, oils, pollen (J. Cizmarik, I. Matel, Experentia 15, 713 (1970)), flavonoids (V. S. Bankova, S. S. Popov, N. L. Marekov, J. Nat. Prod. 46, 471 (1983)), and polyphenolic acids (J. Cizmarik, supra). Together these substances provide properties which permit its natural use by the honeybee as a hive cement or glue (G. Toth, Am. Bee J. 125, 337 (1985)).

Some of the observed biological activities may be traced to identified chemical constituents such as caffeic acid (J. Cizmarik, supra), which is a reported antimicrobial and anti-inflammatory agent (V. S. Bankova, supra). However, it is difficult to generalize such relationships since the composition of propolis varies with the flora of a given area, the time of collection and contaminants from collection (G. Toth, supra). Ethyl ether extracts of propolis have previously been demonstrated to be cytostatic to KB and HeLa cell lines (B. Hladon et al., Arzneim-Forsch./Drug Res. 30, 1847 (1980)), however the components responsible for this interesting activity were not defined.

The invention described herein concerns a compound present in propolis which is at least partially responsible for its reported cytostatic properties. It represents the most active component as judged by the assay employed in its study (cytostatic towards Ltk⁻ cells). The compound has been identified as caffeic acid phenethyl ester (CAPE) and a one-step synthesis method has been developed which is amenable to large scale preparation. Through investigations of CAPE's cytostatic properties uncovered several differential effects. For example, human tumor cell lines displayed a significantly greater sensitivity to the action of CAPE than analogous normal lines. Additionally, CAPE has been found to possess anti-inflammatory activity. Phenethyl alcohol and caffeic acid, the most obvious metabolic products of CAPE, displayed none of the aforementioned activities.

SUMMARY OF THE INVENTION

The present invention concerns a compound having the structure:

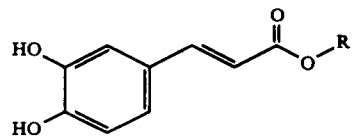

wherein R comprises a phenethyl, butyl, hexyl, or ethyl group.

The invention also provides a method of producing the compound which comprises contacting caffeic acid with an alcohol having the formula R—OH, wherein R comprises a phenethyl, butyl, hexyl or ethyl group, so as to produce the compound and recovering the compound so produced. Another aspect of the invention concerns a method of producing the compound from propolis which comprises contacting the propolis with a solvent so as to form an extract comprising the compound and treating the extract so as to recover the compound.

Additionally, the present invention provides a method of treating inflammation in a subject which comprises administering to the subject an effective anti-inflammatory amount of the compound so as to suppress the inflammation. Another embodiment of the invention provides a method for substantially inhibiting the growth of transformed cells without substantially inhibiting the growth of normal cells which comprises treating a population of cells which include both the transformed and normal cells with an effective inhibiting amount of the compound so as to substantially inhibit the growth of the transformed cells.

μCi [³H]thymidine for 5 hours. For further details referred to M. Eisinger, O. Marko, S. I. Ogata, L. J. Old, Science 229, 984 (1985).

Figure 4:
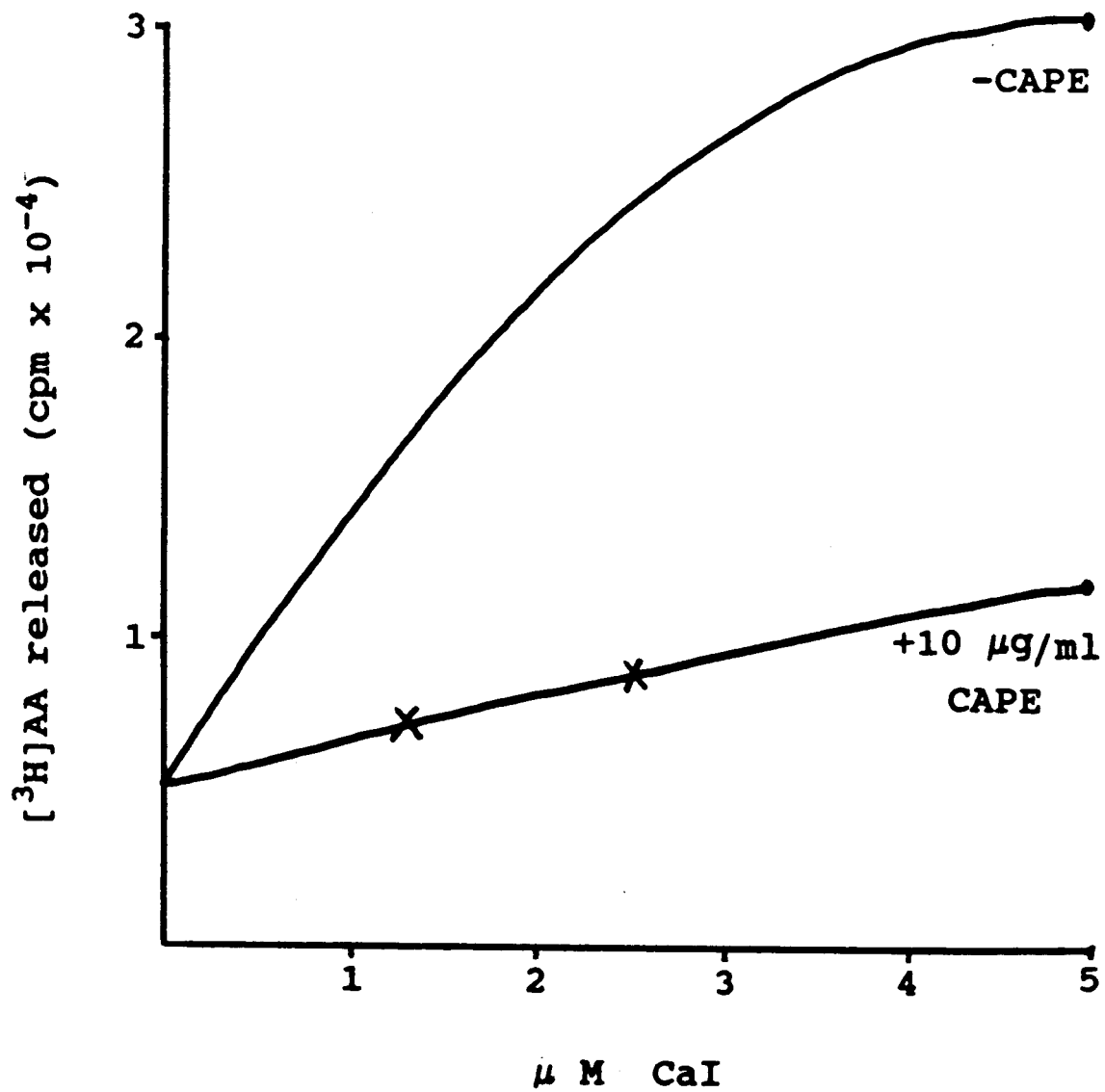

FIG. 4 Effect of CAPE on CaI stimulated release of [³H] arachidonic acid.

DETAILED DESCRIPTION OF THE INVENTION

This invention concerns a compound having the structure:

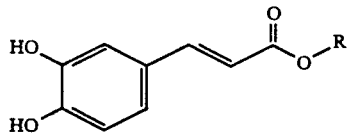

wherein R is an alkyl or arylalkyl group.

Preferably R is a phenethyl, butyl, hexyl or ethyl group. Especially useful are compounds having the structure:

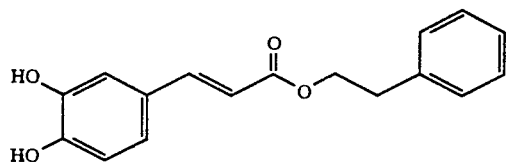

The invention also provides a method of producing the compound which comprises contacting caffeic acid with alcohol having the formula R—OH, wherein R is the same as previously defined, so as to produce the compound and recovering the compound so produced. In embodiments where R is a phenethyl group, the method of producing the compound comprises contacting caffeic acid with phenethyl alcohol. The contacting may be effected in an organic solvent, such as benzene. The contacting also may be effected in the presence of a catalyst, such as p-toluene sulfonic acid. In the most preferred embodiment, the contacting is effected by adding the caffeic acid, phenethyl alcohol and p-toluene sulfonic acid to benzene, producing a suspension and treating the suspension so as to produce the compound. The contacting is especially effective when performed at a temperature of about 100° C. Recovering may be effected by extraction, filtration, evaporation or recrystallization. The invention also provides a method for producing the compound from propolis which comprises contacting the propolis with a solvent so as to form an extract comprising the compound and treating the extract to recover the compound. In the practice of this embodiment, treating may comprise filtration, evaporation or extraction. Preferably, treating comprises extracting the propolis with hexane, recovering the resulting hexane extract then extracting the hexane extract with toluene, recovering the resulting toluene extract, then extracting the toluene extract with ethyl acetate and recovering the resulting ethyl acetate extract. Treating may further comprise purifying the recovered ethyl acetate extract by means such as of thin layer chromatography or reverse phase high pressure liquid chromatography or a combination of both.

Another aspect of the invention concerns a method for treating inflammation in a subject which comprises administering to the subject an effective anti-inflammatory amount of the compound so as to suppress the inflammation. Especially preferred is a method for treating inflammation in the subject which comprises administering to the subject an effective anti-inflammatory amount of the compound having the structure:

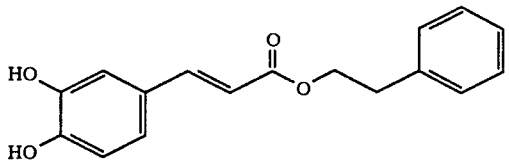

Additionally, the invention provides a method for substantially inhibiting the growth of transformed cells without substantially inhibiting the growth of normal cells which comprises treating a population of cells which include both transformed and normal cells with an effective inhibiting amount of the compound so as to substantially inhibit the growth of the transformed cells. Especially preferred is a method which comprises treating the population of cells with an effective inhibiting amount of the compound having the structure:

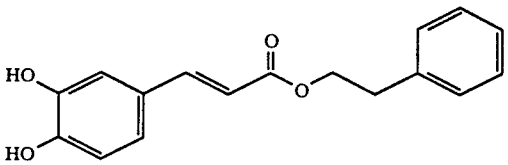

In the practice of the present invention, the transformed cells may comprise carcinoma or melanoma cells. In the preferred embodiments, the subJect is a human and the transformed cells are human carcinoma or melanoma cells, such as human breast carcinoma cells, colon carcinoma cells, renal carcinoma cells, or melanoma cells SK-MEL-28 or SK-MEL-170.

This invention is illustrated in the Experimental Discussion and Experimental Detail sections which follow. These sections are set forth to aid in an understanding of the invention but are not intended to, and should not be construed to, limit in any way the invention as set forth in the claims which follow thereafter.

Experimental Discussion

Propolis was obtained from Mr. Chaim Kalman, Bee FarmHoney, Israel, and was collected from within hives located on the Carmen Mountains. It was received in the form of hard, brown lumps (approximately 2 cm in diameter) which were chopped, extracted with 80% EtOH/H₂O (1.51, 2 d), suction filtered and evaporated (in vacuo) to yield a golden brown solid. This extract displayed cytostatic activity in Ltk⁻ cells at 50 μg/ml. The EtOH extract was dissolved in 80% MeOH/H₂O (400 ml) and subjected to a series of sequential extractions with hexane (6×80 ml), toluene (4×80 ml), and EtOAc (4×100 ml). All organic layers were dried, evaporated and submitted for Ltk⁻ testing (along with the residue from the aqueous layer). The EtOAc extract exhibited at least twice the cytostatic activity as the other fractions (100% inhibition at below 65 μg/ml). Subsequent purifications of the EtOAc extract by preparative TLC (7% i-PrOH/C₂Cl₂ then 4% i-PrOH/CH₂Cl₂) yielded two increasingly active fractions, with the latter exhibiting 100% Ltk⁻ inhibition at 40 μg/ml.

Figure 1:
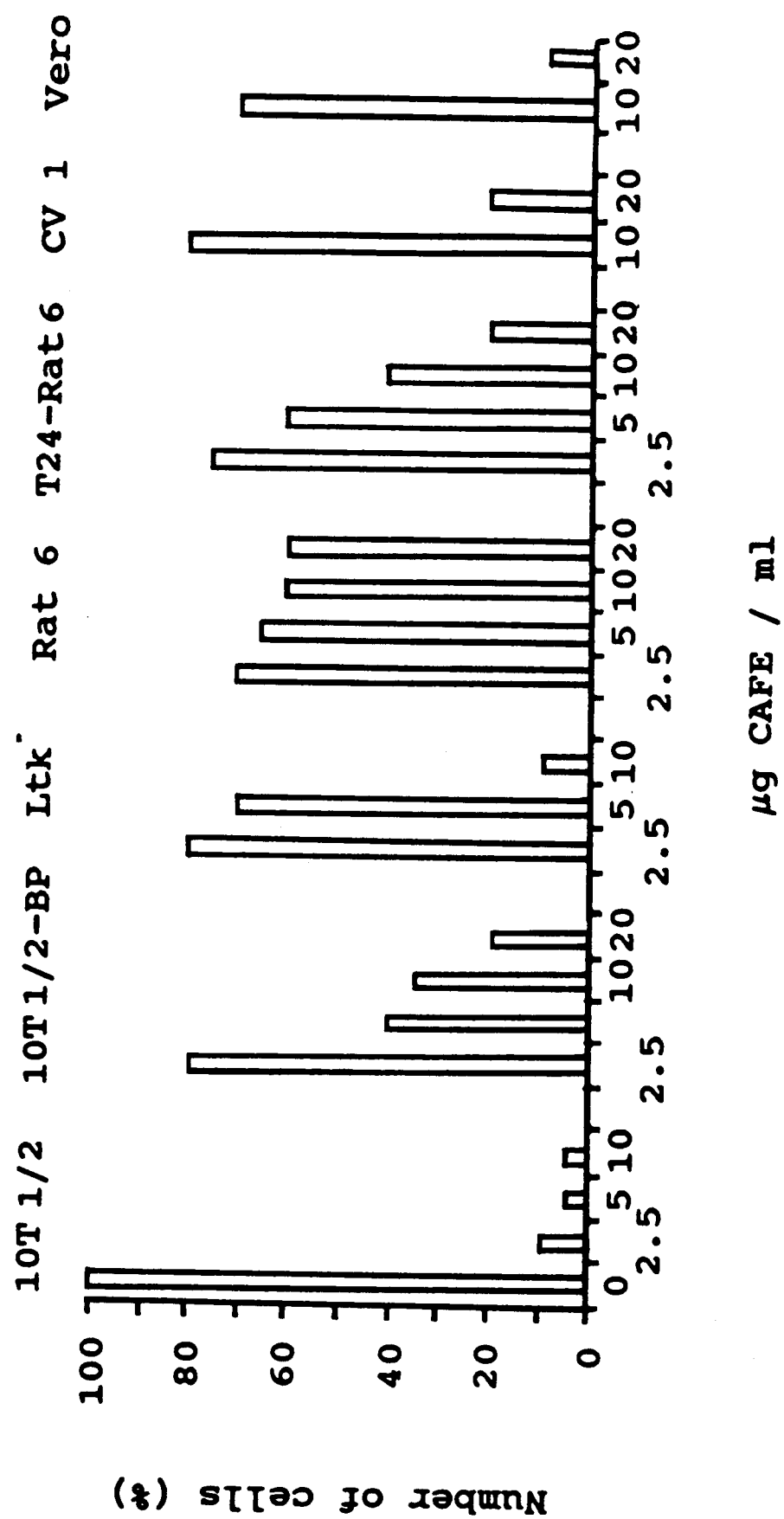
FIG. 1. The effect of increasing concentrations of CAPE on various cultured cell lines. Referred to the text for a description of each cell type and experimental details.

Reversed phase HPLC separation of this latter fraction (Column: IBM-$C_{18}$, 10×250 mm, 5 μ: MeOH/MeCN/THF/$H_2O$—25:35:3.5:36.5; 1.8 ml/min; 213 nm detection) yielded a pure compound (retention time=16.8 min; TLC (SiO$_2$): 4% i-PrOH/$CH_2Cl_2$, $R_f$=0.25, 366 nm illumination—blue fluorescence) which displayed the following Ltk⁻ cytostatic activities (% inhibition in parentheses) (these value are semi-quantitative, as only minute quantities of the natural compound were available; more quantitative values, acquired with synthetic CAPE, are provided in FIG. 1) - 10 μg/ml (20%), 20 μg/ml (80%), 30 μg/ml (95%). The chemical structure of this compound was spectroscopiallly determined to be caffeic acid phenethyl ester (CAPE), and displayed the following characteristics: UV (MeOH): 325 nm (ε 16,200), 300 (sh, 12,500), 245 (9,700), 235 (9,700); IR (KBr): 3490 cm$^{-1}$ (OH's), 1685 (C=O); HR-MS (EI): $C_{17}H_{16}O_4$, m/z 284.1080, calcd 284.1049 (M+), major fragments—180, 163, 104, 91, 77. $^1$H nmr data (250 MHz, acetone-$d_6$): δ8.4–8.2 (brs, 2 H, OH's) 7.52 (d, J=15.9 Hz, 1 H, H$^7$), 7.31–7.15 (m, 5 H, H$^{13-17}$), 7.15 (d, J=2.1 , 1 H, H$^2$), 7.03 (dd, J=8.2, 2.1, 1 H, H$^6$), 6.86 (d, J=8.2, 1 H, H$^5$), 6.26 (d, J=15.9, 1 H, H$^8$), 4.34 (t, J=7.0, 2 H, H$^{10}$), 2.98 (t, J=7.0, 2 H, H$^{11}$); $^{13}$C nmr (62.89 MHz, CDCl$_3$): δ167.8 (s), 146.5 (s), 145.2 (d), 144.0 (s), 137.8 (s), 128.9 (d), 128.5 (d), 127.6 (s), 126.6 (d), 122.5 (d), 115.5 (2d's), 114.5 (d), 65.2 (t), 35.3 (t).

Direct acid-catalyzed (p-toluene sulfonic acid) esterification of caffeic acid (CA) with phenethyl alcohol (molar ratios 1:15) in benzene (refluxing, 3–4 days, water removed by a Dean-Stark trap), instead of leading to self-condensation of CA, proved to be the most efficient synthetic route to CAPE. Prior to the success of direct esterification, several attempts to prepare CAPE via conventional protection/deprotection method were carried out with inferior results. Following work-up, excess phenethyl alcohol was removed by Kugelrohr distillation (60° C., less than 0.1 mm Hg) and pure CAPE was obtained as needles by recrystallization (either benzene or H$_2$O, 40% yield, mp =126°–128° C.). Chromatographic, spectroscopic and cytostatic properties of the natural and synthetic CAPE were identical.

Cytostatic activities of synthetic CAPE were tested by observing its effect on the growth of a number of different cell types in culture. Cells were cultured in Dulbecco's modified Eagle's medium supplemented with 5–10% calf serum and maintained at 37° C. in 5% CO$_2$. Approximately 3–4×10$^5$ cells were plated in 60 mm Petri dishes. Concentrated stock solutions of CAPE, CA and phenethyl alcohol (hydrolysis products of CAPE) were prepared in EtOH. After 24 hours, the cells were supplied with fresh medium spiked with various amounts of these solutions or corresponding amounts of EtOH (control). Caffeic acid, phenethyl alcohol and ethanol were never observed to significantly affect the growth of any cell line tested. Approximately 48 hours subsequent to treatment, the cells on individual plates were counted by Coulter counter or fixed and stained with Giesma. Results from the various cell lines are summarized in FIG. 1. Mouse cells (C3H 10T½ and Ltk⁻) appeared most sensitive, with concentrations as low as 2.5 μg/ml CAPE effectively blocking the growth of 10T½ cells. Interestingly, benzo(a)pyrene transformed 10T½ cells exhibited an increased resistance to CAPE's action, requiring up to 20 μg/ml CAPE for an 80% growth inhibition. Normal Rat 6 cells and those transformed by T24 oncogene were both less sensitive than the murine lines. Similarly, the growth of two monkey cell lines, CV1 and Vero, suffered severe inhibition only at concentrations of CAPE greater than 10 μg/ml.

Figure 2:
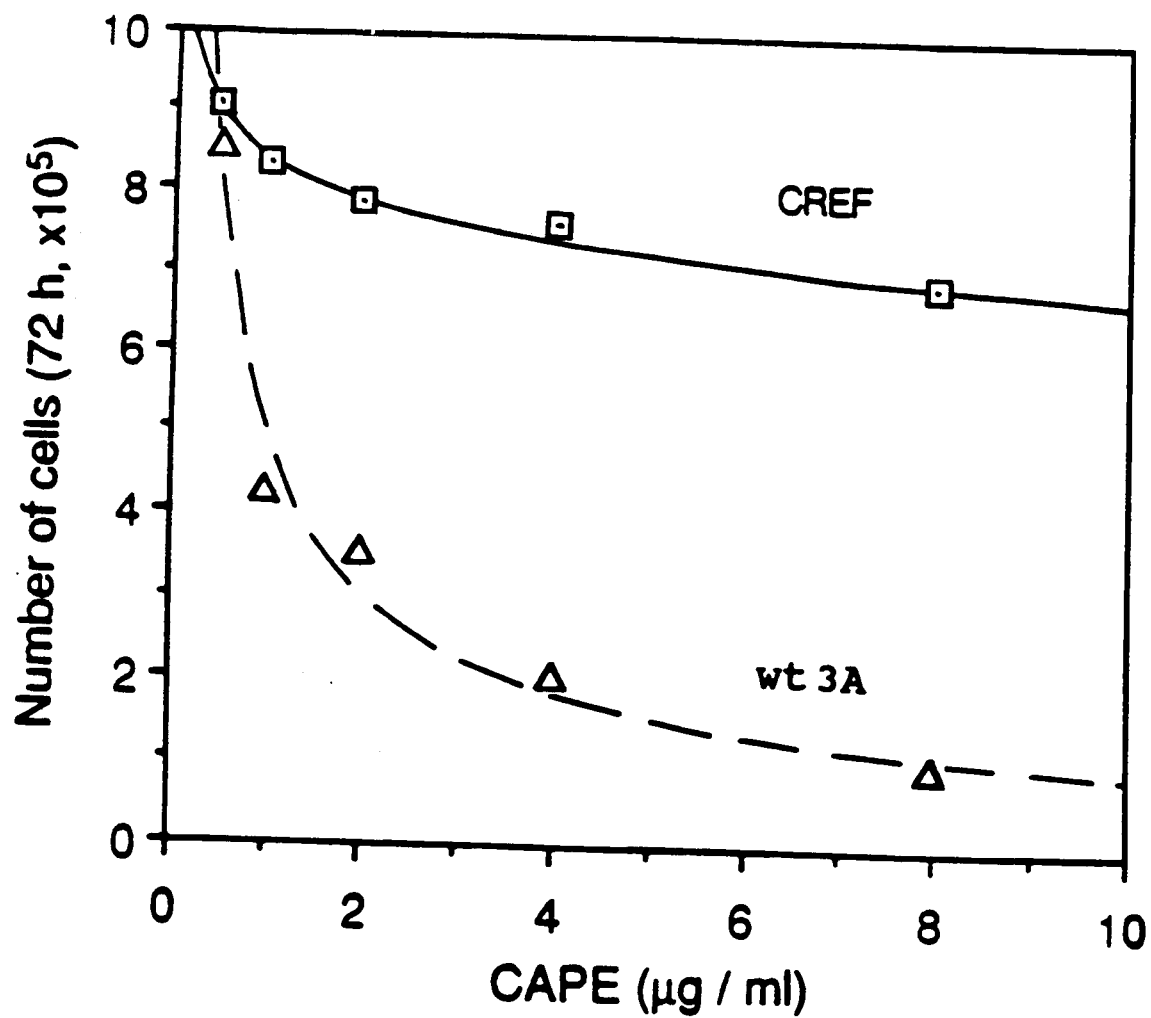
FIG. 2. Effect to CAPE on the growth of CREF (normal rat) and wt3A (adenovirus transformed CREF) cells.

The differential effect of CAPE on the growth of normal and transformed cells was further investigated with a recently isolated cloned cell line of Fischer rat embryo fibroblasts (CREF) and its counterpart, transformed by adenovirus serotype 5 (wt3A) (P. B. Fisher, L. E. Babiss, I. B. Weinstein, H. S. Ginsberg, Proc. Natl. Acad. Sci. U.S.A. 79, 3527 (1982)). The transformed cells were identified by their altered morphologies and the presence of adenovirus DNA sequences in their genomes (Id.). The effects of various concentrations of CAPE on the growth of CREF and wt3A lines after 72 h are summarized in FIG. 2. At concentrations of CAPE as high as 8 μg/ml, approximately 75% of the CREF cells remained unaffected, yet under the same conditions, growth of the wt3A cells was inhibited by nearly 90%. Hence, the presence of CAPE elicited a marked differential effect on the growth of these two rat cell lines which also displayed important difference in their biological properties. Unlike CREF cells, morphologically transformed cells exhibited higher saturation densities and were capable of anchorage-independent growth. Because the cytostatic mechanism of CAPE is not understood at present, any explanation for the differential effects of this inhibitor upon the growth of normal CREF and transformed wt3A cells remains purely speculative.

Figure 3A:
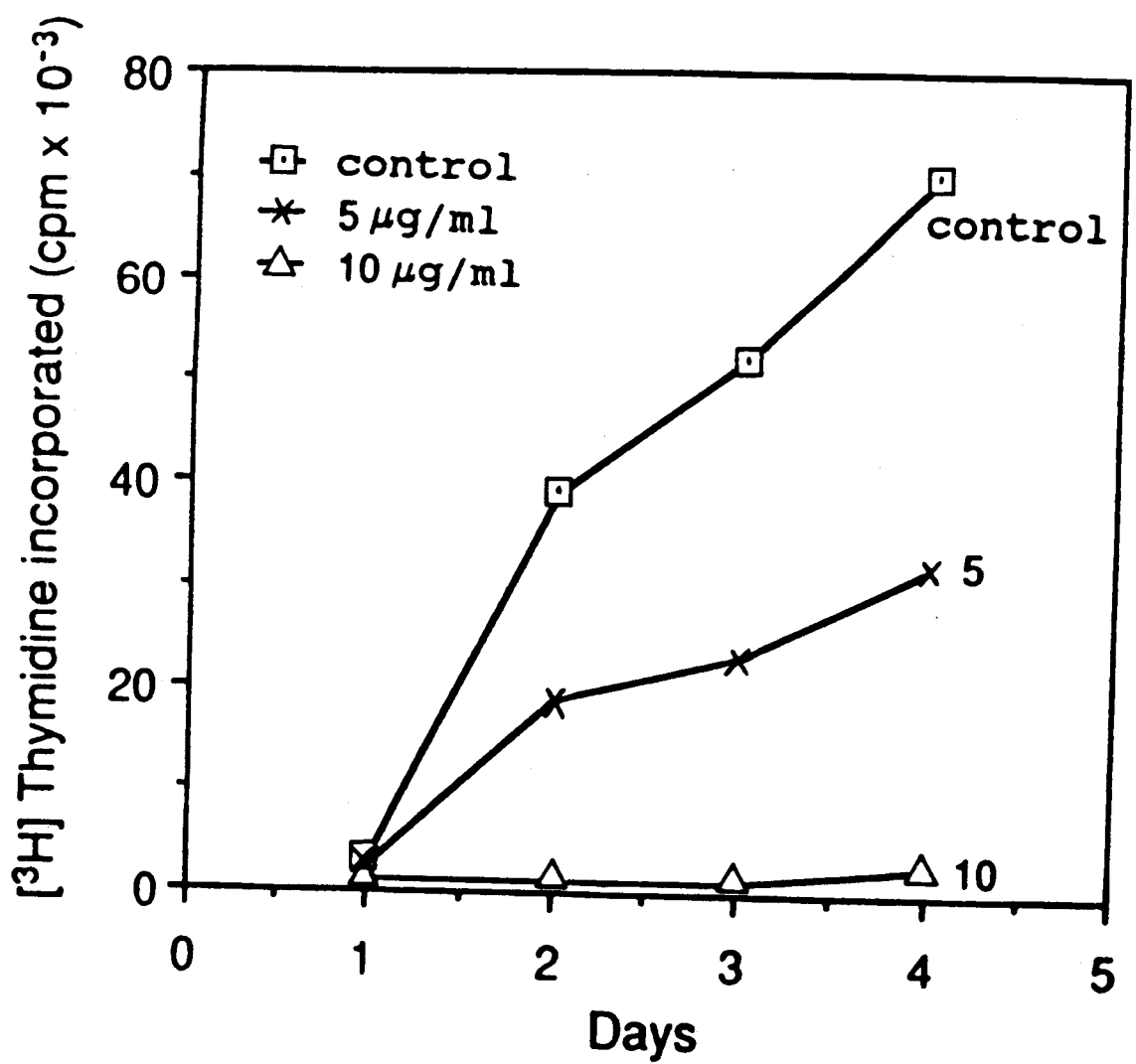
FIG. 3. Effect of CAPE on the rate of division (as measured by incorporation of [³H]thymidine) of (a) human MCF-7 breast carcinoma, (b) human SK-MEL-28 melanoma cells and (c) human SK-MEL-170 melanoma cells. Cells were maintained in Eagle's minimal essential medium (MEM) with Earle's salts and 10% fetal bovine serum. The cells were seeded in the same medium in tissue culture cluster plates (96 flat bottom wells) at $10^3$ cells/well. Twenty-four hours later the cultures were washed and different concentrations of CAPE were added to each well in triplicate. Labelling of the cells was accomplished by incubating with 0.5
Figure 3B:
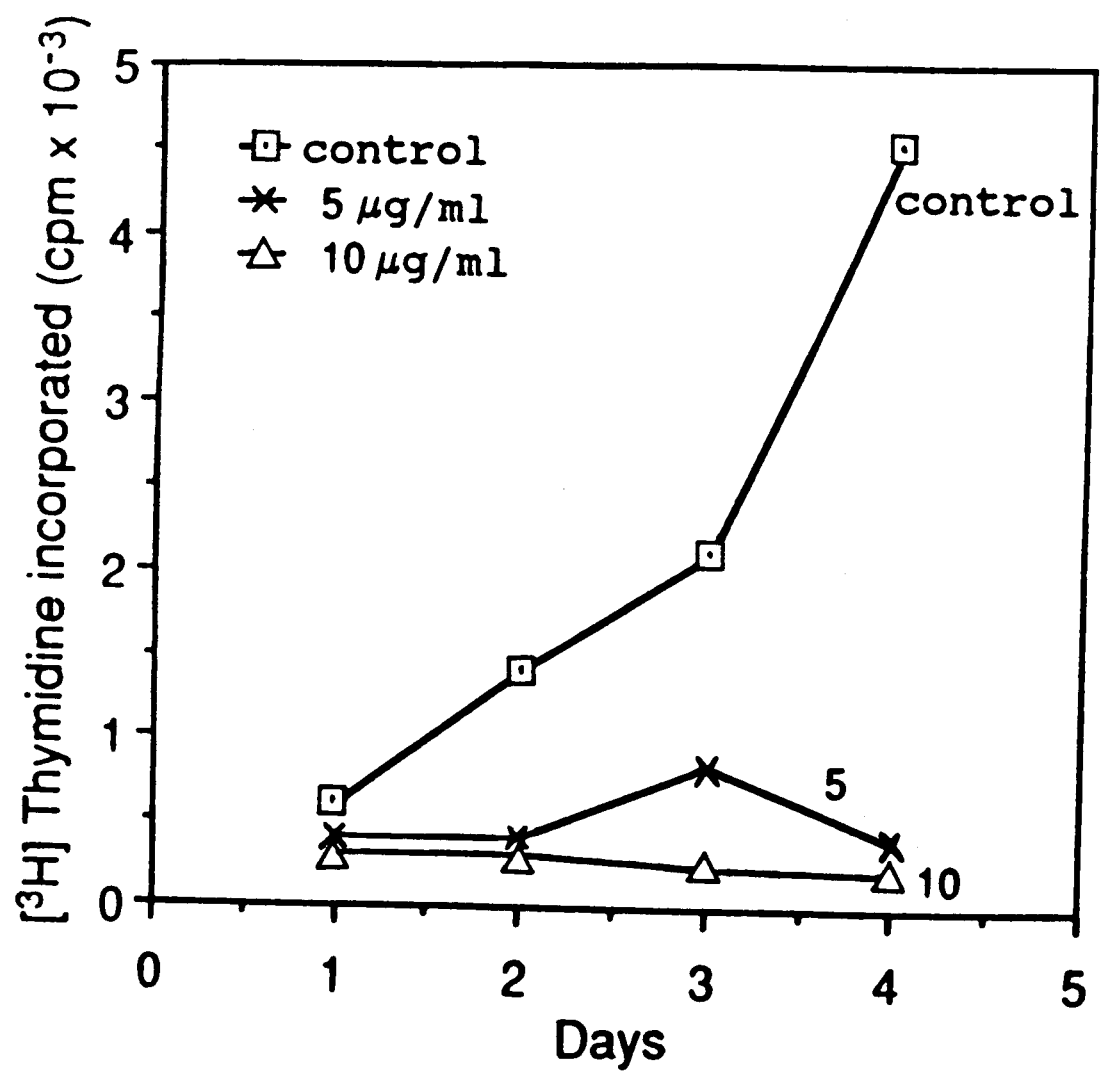
Figure 3C:
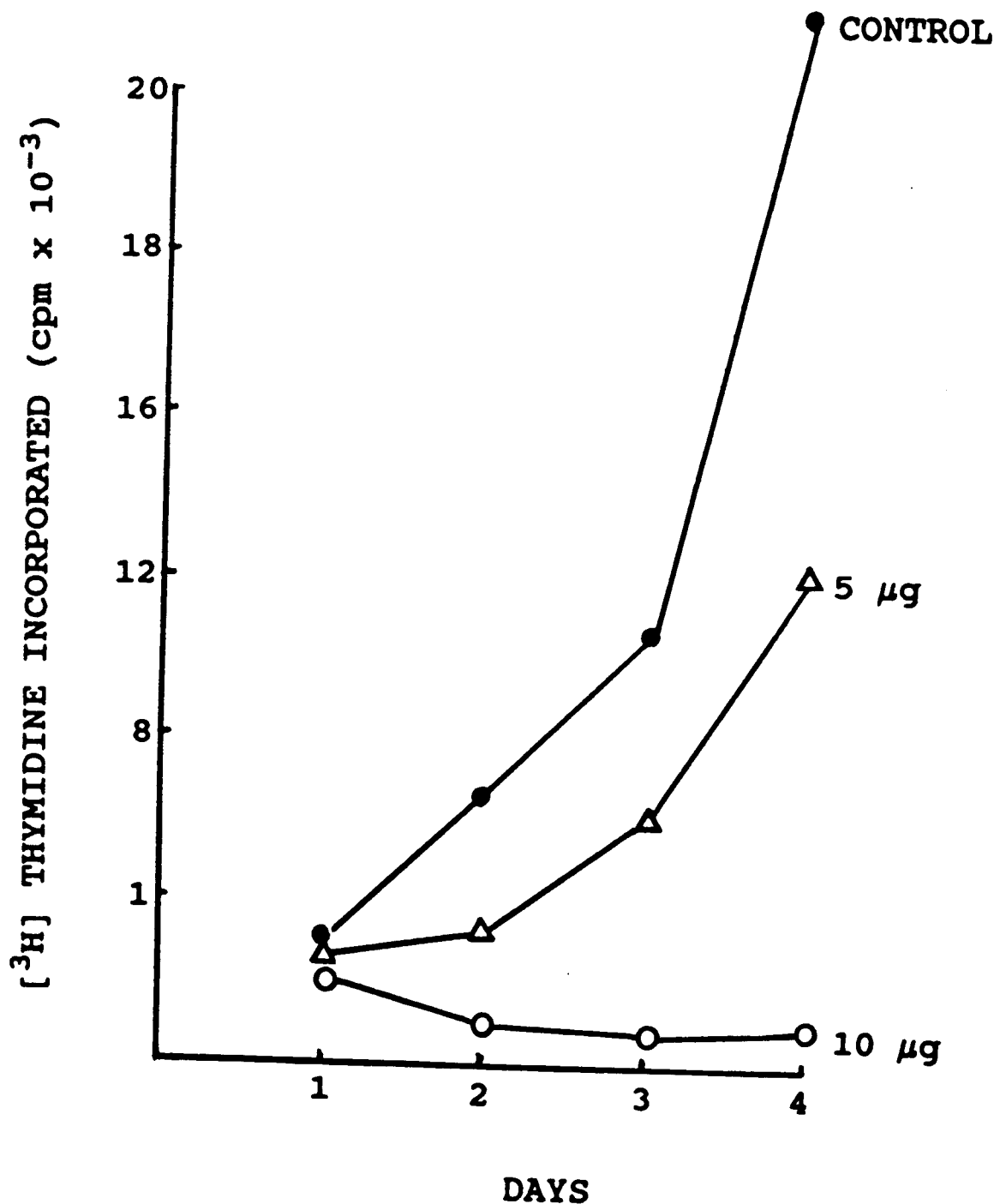

The effect of CAPE on human cancer cells was tested by measuring incorporation of [$^3$H]thymidine into the DNA of human breast carcinoma (MCF-7) and melanoma (SK-MEL-28 and SK-MEL-170) cell lines in culture (M. Eisinger, O. Marko, S.-I. Ogata, L. J. Old, Science 229, 984 (1985)). FIG. 3a reveals that 5 μg/ml CAPE inhibits incorporation of [$^3$H]T into the DNA of human breast carcinoma MCF-7 by approximately 50% and is completely blocked by concentrations of 10 μg/ml. Even more dramatic effects were observed with the two melanoma lines, SK-MEL-28 and SK-MEL-170. FIG. 3b and FIG. 3c illustrate the effect of different concentrations of CAPE on the incorporation of [$^3$H]T into SK-MEL-28 and SK-MEL-170 cells, respectively. At 5 μg CAPE/ml the cells displayed minimal incorporation and were completely inhibited at 10 μg/ml. Similar inhibitions were observed for HT29 colon and renal carcinoma lines (not shown). The effect of CAPE on normal 1434 fibroblasts and melanocytes was significantly less. Incorporation of [$^3$H]T into these normal cells was inhibited by only 50% at concentration of CAPE up to ten times greater (50 μg/ml, data not shown). These differential effects were reminiscent of those observed with the normal CREF and transformed wt3A rat cells.

The ready accessibility of analogs and labelled versions of CAPE will simplify further investigations into its mode of action, and may lead to an understanding of the observed differential effects on a molecular level. Furthermore, such studies with CAPE and other cytostatic compounds may provide a clearer insight into the molecular events responsible for the dissimilar biological properties exhibited by transformed and normal cells. Because the cytostatic action of CAPE is more dramatic on transformed cells, one may reasonably assume that it is at least partly responsible for the claimed carcinostatic properties of propolis.

Experimental Details

Effect of CAPE on cell growth:

Cell culture: Mouse Ltk⁻ and 10T½ cells, monkey CVI and Vero cells, a clone of rat embryo fibroblast cell line—CREF and a wild type adenovirus transformed CREF cell line—wt3A were grown in Dulbecco's modified Eagle's medium supplemented with 5–10% calf serum at 37° C. with 5% CO. About $3-4\times10^5$ cells were plated in 60 mm dishes After 24 hours the cells were fed with fresh medium containing various amounts of CAPE. A concentrated stock solution (10 mg/ml of CAPE) was prepared in ethanol. The control plates were simultaneously treated with equal volume of ethanol. After 48 hours following the treatment the cells in individual plates were either counted by Coulter counter or fixed and stained with Giemsa for estimation of relative toxicity of CAPE.

It is evident that the mouse cells (10T½ and Ltk⁻) are the most sensitive to CAPE At 5 μg/ml concentration there is 95% inhibition of the growth of 10T½ cells. The monkey cells (CVI and Vero) are less sensitive. Only at 20 μg/ml is the growth of these cells inhibited almost completely. Interesting is the sensitivity of rat cells to the action of CAPE. Normal CREF cell line at 10 μg/ml is inhibited only by 30%. However, the adenovirus transformed cell line wt3A is highly inhibited at 5.0 μg/ml (82%) already and at 10 μg/ml practically there is a complete inhibition of the growth of these transformed cells.

Effect of CAPE on melanocyte and melanoma cells in culture:

Foreskin melanocytes were maintained in Earle's minimal essential medium (MEM) with Eagle's salts: 0.01 mM nonessential amino acids, 2 mM L-glutamine containing penicillin (100 unit/ml), streptomycin (0.1 mg/ml) and Fungizone (0.25 μg/ml); 10 percent fetal bovine serum (cMEM), 12-0-tetradecanoyl phorbol 12-acetate (TPA) (10 ng/ml) and cholera toxin $10^{-8}$M for 15 passages, according to M. Eisinger, O. Marko, S.-I. Ogata, L. J. Old, Science 229, 984 (1985). They were then seeded in the same medium in tissue culture cluster plates (96 flat bottom wells) at $5\times10^3$ per well.

Twenty-four hours later, the cultures were washed three times with MEM (not containing TPA and cholera toxin) and incubated for 4 hours. Cells were then fed at 3-day intervals with cMEM containing CAPE in concentrations as indicated. Melanoma cell lines SK-MEL-28 and SK-MEL-170 in passage 40 were seeded at $1\times10^3$ per well under the same conditions as the melanocytes but without TPA and cholera toxin. Labeling of melanocytes and melanomas was performed with [³H]thymidine (10 μCi/ml) for 6 hours at indicated time periods after the initial addition of CAPE. After labeling, the cells were washed three times with phosphate-buffered saline (PBS), dislodged from the wells by trypsin-EDTA solution, and counted in Hydrofluor with a scintillation counter.

Cells for the release of arachidonic acid:

Human keratinocytes were isolated and grown according to the system of Elinger et al., PNAS, 76, 5340 (1979), in 12 well plates in minimal essential medium (KM) with Earle's salts (Gibco) plus non-essential amino acids (0.01 mM), 2 mM L-glutamine, hydrocortisone (0.4 μg/ml), penicillin (100 U/ml), streptomycin (0.1 mg/ml) and fungizone (2.5 μg/ml). The growth medium included 10% heat-inactivated fetal calf serum (FCS) (KM+10). Cells were isolated from normal human breast skin obtained from surgical specimens. The skin was cut into small discs and exposed for a 12–14 hour period to a 0.25% trypsin solution at 4° C. The tryptic action was stopped by the addition of 20% FCS. The epidermis from each disc was peeled from the dermis and the epidermal discs were pooled. A single cell suspension of epidermal cells was produced by vigorous trituration in trypsin: EDTA solution (0.05%:0.02%). The trypsin: EDTA solution was inactivated with serum. Cells were centrifuged, the trypsin: EDTA was removed and the cells were counted. After dilution with growth medium (pH 7.4–7.6) cells were seeded at appropriate densities ($1.2-1.4\times10^5$/cm²). Cells were fed twice weekly and maintained at 37° C. in moisturized room air with 5% $CO_2$. Cells were utilized in primary passage.

Assay for the release of arachidonic acid (AA):

Cells were grown in plastic dishes until approximately 90% confluency (9–14 days). At a density of $2-3\times10^5$/cm² cells were pre-labelled with [³H]AA 2 μCi/ml in KM+10. The cells were allowed to incorporate the radiolabel for a 20–24 hour period under the incubation conditions outlined above. After the labelling period, the labelling media was removed and the cells were washed three times with assay medium. The pre-labelled cells were then treated with various concentrations of either calcium ionophore (A 23187) and CAPE or only CAPE in triplicate wells. Media containing equivalent amounts of solvents without CAPE served as control. The treated cells were incubated at 37° C. for 2 hours. The media were then removed, centrifuged at 12000 r.p.m for 5 minutes and an aliquot was assayed by liquid scintillation to determine the total c.p.m. released. All assays were done with triplicate dishes for experimental and control conditions.

When human keratinocytes were pre-labelled with [³H]AA they incorporated 60–80% of the label from the medium during 20–24 hour period. FIG. 4 shows that calcium ionophore stimulate the release of [³H]AA. However, in the presence of 10 μg/ml CAPE there was almost no stimulation of the release of AA. Since inhibitors of arachidonic acid deacylation and metabolism applied to mouse skin inhibit the inflammatory response to phorbol ester, it is assumed that CAPE has similar anti-inflammatory effect.

What is claimed is:

1. A purified compound having the structure:

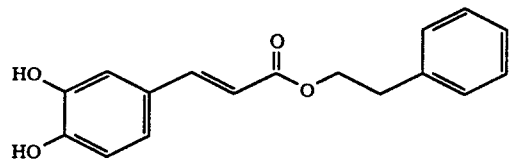

2. A method of producing the compound of claim 1 which comprises contacting caffeic acid with a phenethyl alcohol so as to produce the compound and recovering the compound so produced.

3. A method of claim 2, wherein contacting is effected in an organic solvent.

4. A method of claim 3, wherein the solvent is benzene.

5. A method of claim 2, wherein contacting is effected in the presence of a catalyst.

6. A method of claim 5, wherein the catalyst is p-toluene sulfonic acid.

7. A method of claim 6, wherein contacting is effected by adding the caffeic acid, phenethyl alcohol, and p-toluene sulfonic acid to benzene to produce a suspension, and treating the suspension so as to produce the compound.

8. A method of claim 7, wherein the contacting is effected at a temperature of about 100° C.

9. A method of claim 7, wherein the recovering comprises extraction, filtration, evaporation or recrystallization.

10. A method of producing the compound of claim 1 from propolis which comprises contacting the propolis with a solvent so as to form an extract comprising the compound and treating the extract so as to recover the compound.

11. A method of claim 10, wherein the treating comprises filtration, evaporation or extraction.

12. A method of claim 11, wherein the treating comprises extracting the propolis with hexane, recovering the resulting hexane extract, then extracting the hexane extract with toluene, recovering the resulting toluene extract, and then extracting the toluene extract with ethyl acetate and recovering the resulting ethyl acetate extract.

13. A method of claim 12 further comprising purifying the recovered ethyl acetate extract.

14. A method of claim 13, wherein the purifying of the ethyl acetate extract comprises thin layer chromatography.

15. A method of claim 14, wherein the purifying further comprises reversed phase high pressure liquid chromatography.

16. A method for treating inflammation in a subject which comprises administrating to the subject an effective anti-inflammatory amount of the compound of claim 1 so as to suppress the inflammation.

17. A method for substantially inhibiting the growth of transformed cells without substantially inhibiting the growth of normal cells which comprises treating a population of cells which include both transformed and normal cells with an effective inhibiting amount of the compound of claim 1 so as to substantially inhibit the growth of the transformed cells.

18. A method of claim 17, wherein the transformed cells are human carcinoma or melanoma cells.

19. A method of claim 18, wherein the transformed cells are human breast carcinoma cells.

20. A method of claim 18, wherein the transformed cells are human melanoma cells SK-MEL-28 or SK-MEL-170.

21. A method of claim 18, wherein the transformed cells are colon or renal carcinoma cells.

* * * * *